(12) United States Patent
Calhoun et al.

(10) Patent No.: US 7,312,049 B2
(45) Date of Patent: Dec. 25, 2007

(54) TOTAL AMINO ACID STABILIZATION DURING CELL-FREE PROTEIN SYNTHESIS

(75) Inventors: Kara Anne Calhoun, Mountain View, CA (US); James Robert Swartz, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 11/447,367

(22) Filed: Jun. 5, 2006

(65) Prior Publication Data

US 2007/0004001 A1    Jan. 4, 2007

Related U.S. Application Data

(60) Provisional application No. 60/690,571, filed on Jun. 14, 2005.

(51) Int. Cl.
*C12P 21/06* (2006.01)
*C12N 1/20* (2006.01)

(52) U.S. Cl. .................. 435/68.1; 435/69.1; 435/252.3

(58) Field of Classification Search ............... 435/68.1, 435/69.1, 252.3
See application file for complete search history.

(56) References Cited

U.S. PATENT DOCUMENTS

| | | |
|---|---|---|
| 6,168,931 B1 | 1/2001 | Swartz et al. |
| 6,337,191 B1 | 1/2002 | Swartz et al. |
| 6,559,176 B1 | 5/2003 | Bassler et al. |
| 2002/0081660 A1 | 6/2002 | Swartz et al. |
| 2004/0209321 A1 | 10/2004 | Swartz et al. |

FOREIGN PATENT DOCUMENTS

| | | |
|---|---|---|
| WO | WO 00/55353 | 9/2000 |
| WO | WO 2004/016778 A1 | 2/2004 |
| WO | WO 2005/010155 A2 | 2/2005 |

OTHER PUBLICATIONS

Metabolic Engineering, Issue 3, Jul. 2004, pp. 197-203; Available on line Apr. 27, 2004.*
Datsenko, K., et al., "One-step inactivation of chromosomal genes in *Escherichia coli* K-12 using PCR products," (2000) *PNAS*, 97(12):6640-6645.
Kim, D., et al., "A highly efficient cell-free protein synthesis from *Escherichia coli*," (1996) *Eur. J. Biochem*, 239:881-886.
Su, et al., "L-serine degradation in *Escherichia coli* K-12: Cloning and sequencing of *sdaA* gene," (1989) *Journal of Bacteriology*, 171(9):5095-5102.
Jewett, M., et al., "Mimicking the *Escherichia coli* cytoplasmic environment activates long-lived and efficient cell-free protein synthesis," (2004) *Published online by Wiley InterScience* (www.interscience.wiley.com, DOI 10/1002/bit.20026.
Kudlicki, W., et al., "High efficiency cell-free synthesis of proteins: refinement of the coupled transcription/translation system," (1992) *Analytical Biochemistry*, 206:389-393.
Michel-Reydellet, N., et al., "Amino acid stabilization for cell-free protein synthesis by modification of the *Escherichia coli* genome," (2004) 6:197-203.
Pratt, J., "Coupled transcription-translation in prokaryotic cell-free systems," (1984) *Transcription and translation: a practical approach*, Hames, B. and Higgins, S., eds., pp. 179-209.
Jewett, M., et al., "Prokaryotic systems for in vitro expression," (2002) *Gene cloning and expression technologies*, Weiner, M. and Lu, Q., eds., pp. 391-411.
Shao, et al., "Sequencing and characterization of the *sdaB* gene from *Escherichia coli* K-12," 91993) *Eur. J. Biochem*. 212:777-784.

* cited by examiner

*Primary Examiner*—Tekchand Saidha
(74) *Attorney, Agent, or Firm*—Bozicevic, Field & Francis LLP; Pamela J. Sherwood

(57) ABSTRACT

Compositions and methods are provided for the enhanced in vitro synthesis of protein molecules, by optimizing the metabolism of amino acids present in the reaction mix, preferably all amino acids in the reaction mixture. By performing synthesis with extracts from genetically modified microbial strains that are deficient in multiple amino acid metabolizing enzymes reduces the enzymatic activities responsible for catalyzing these reactions and improves the overall yield of synthesis.

8 Claims, 3 Drawing Sheets

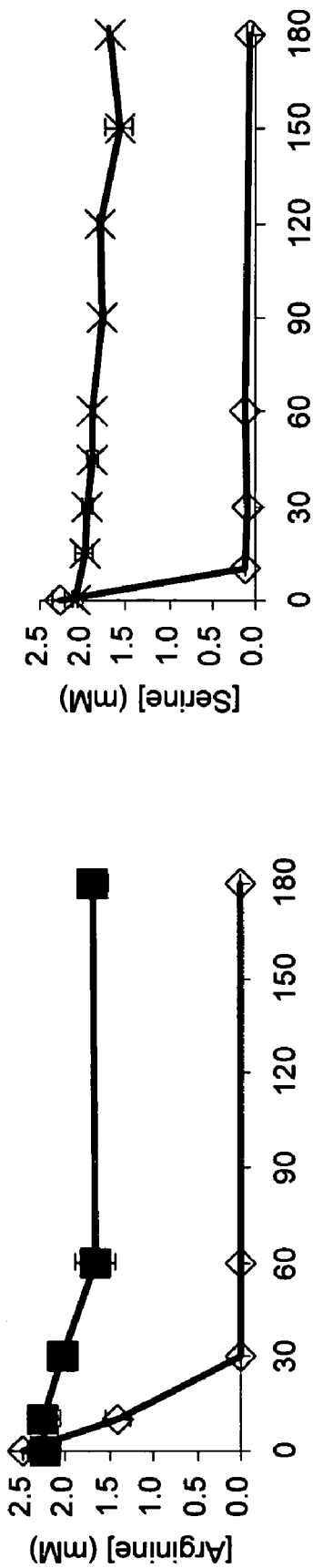
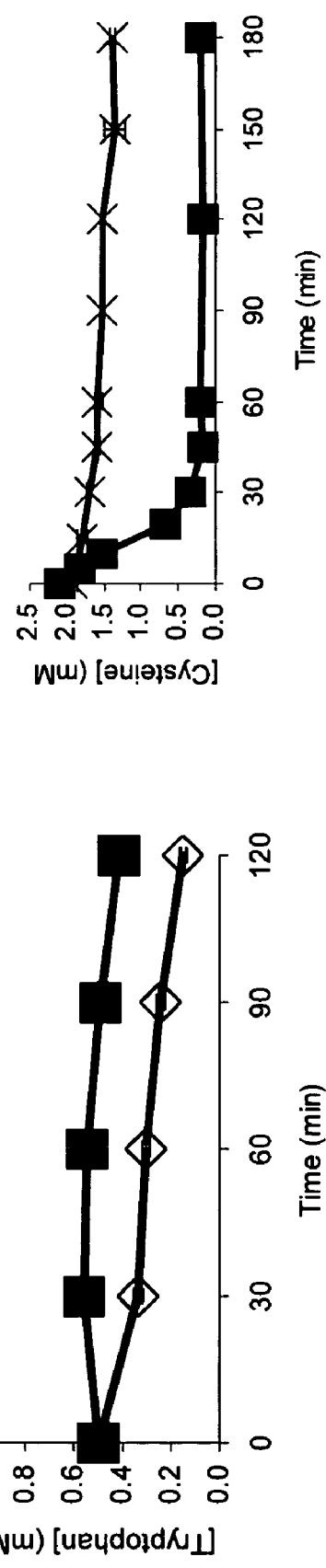
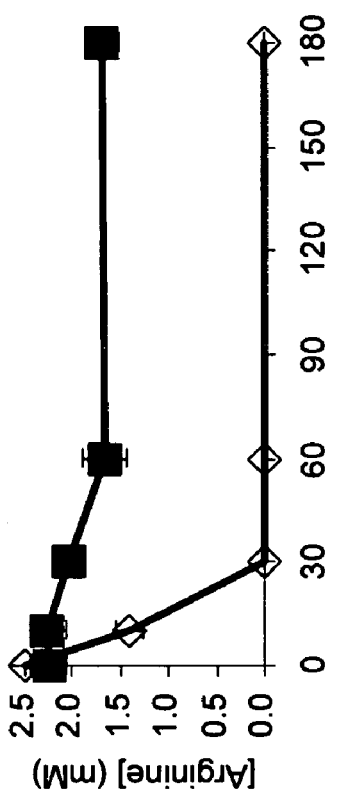
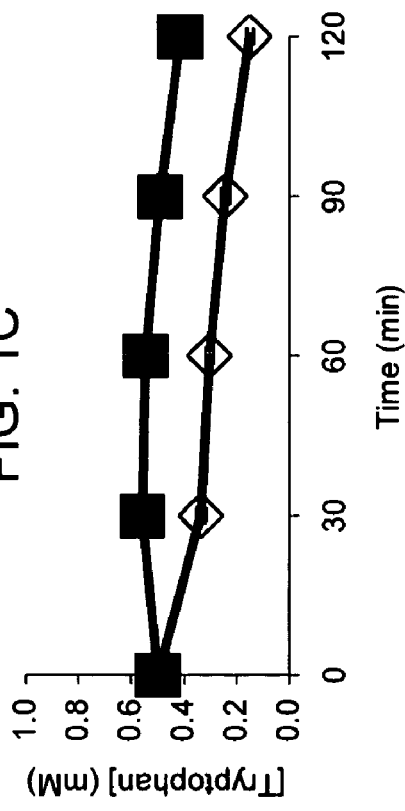
FIG. 1A
FIG. 1B
FIG. 1C
FIG. 1D

TOTAL AMINO ACID STABILIZATION DURING CELL-FREE PROTEIN SYNTHESIS

CROSS-REFERENCE TO RELATED APPLICATIONS

This application claims the benefit of priority to U.S. provisional application 60/690,571, filed Jun. 14, 2005, now expired.

BACKGROUND OF THE INVENTION

Protein synthesis is a fundamental biological process, which underlies the development of polypeptide therapeutics, diagnostics, and catalysts. With the advent of recombinant DNA (rDNA) technology, it has become possible to harness the catalytic machinery of the cell to produce a desired protein. This can be achieved within the cellular environment or in vitro using extracts derived from cells.

Over the past decade, the productivity of cell-free systems has improved two orders of magnitude, from about 5 μg/ml-hr to about 500 μg/ml-hr. This accomplishment has made in vitro protein synthesis a practical technique for laboratory-scale research and provides a platform technology for high-throughput protein expression. It also begins to suggest the feasibility of using cell-free technologies as an alternative means to the in vivo large-scale production of protein pharmaceuticals.

Cell-free protein synthesis offers several advantages over conventional, in vivo, protein expression methods. Cell-free systems can direct most, if not all, of the metabolic resources of the cell towards the exclusive production of one protein. Moreover, the lack of a cell wall in vitro is advantageous since it allows for better control of the synthesis environment. For example, tRNA levels can be changed to reflect the codon usage of genes being expressed. Also, the redox potential, pH, or ionic strength can be altered with greater flexibility than in vivo since we are not concerned about cell growth or viability. Furthermore, direct recovery of purified, properly folded protein products can be easily achieved.

In vitro translation is also recognized for its ability to incorporate unnatural and isotope-labeled amino acids as well as its capability to produce proteins that are unstable, insoluble, or cytotoxic in vivo. In addition, cell-free protein synthesis may play a role in revolutionizing protein engineering and proteomic screening technologies. The cell-free method bypasses the laborious processes required for cloning and transforming cells for the expression of new gene products in vivo and is becoming a platform technology for this field.

Despite all of the promising features of cell-free protein synthesis, its practical use and large-scale implementation has been limited by several obstacles. Paramount among these are short reaction times and low protein production rates, which lead to poor yields of protein synthesis and excessive reagent cost. One of the factors limiting production is the degradation of amino acids. The present invention addresses these issues.

Relevant Literature

Patent documents relating to in vitro protein synthesis include U.S. Pat. No. 6,337,191 B1; U.S. Patent Published Application 20020081660; U.S. Patent Published Application 20040209321; and International Applications WO2004/016778; WO 2005/010155; WO 00/55353; and WO 00/55353.

SUMMARY OF THE INVENTION

Cell-free synthesis of polypeptides is performed in a reaction mixture comprising microbial cell extracts, which provide biological materials such as ribosomes that are necessary for efficient synthesis. However, extracts from conventional microbial strains undesirably degrade components of the reaction mix, including amino acids, through residual enzymatic activity. Improved protein yield is obtained by performing synthesis with extracts from genetically modified microbial strains that are deficient in multiple amino acid metabolizing enzymes. Preferably such a modified cell strain allows for stable levels of all 20 amino acids during a cell-free reaction.

BRIEF DESCRIPTION OF THE DRAWINGS

FIG. 1A-1D: Amino acid concentration during cell-free protein synthesis reaction incubated with different cell extracts. NMR1 (open diamonds, black line), KC1 (filled squares, red line), KC6 (X, green line).

DETAILED DESCRIPTION OF THE EMBODIMENTS

Figure 2A:
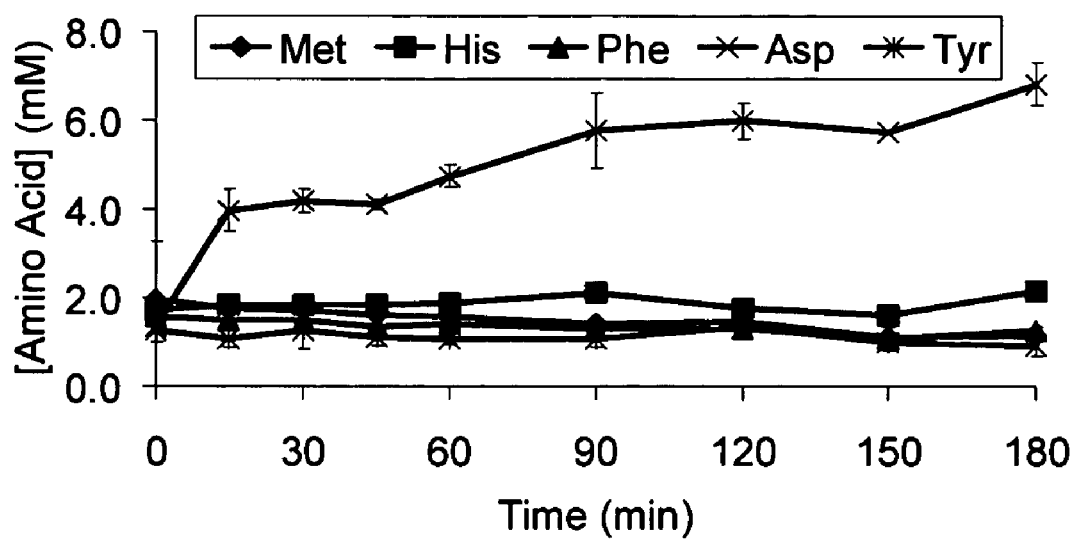
FIG. 2A-2B: Amino acid concentrations of other amino acids using KC6 extract in cell-free reaction.

Compositions and methods are provided for the enhanced in vitro synthesis of protein molecules, by simultaneously optimizing the metabolism of several amino acids present in the reaction mix, preferably all amino acids in the reaction mixture. The concentration of multiple amino acids decreases during conventional reactions due to degradation by enzymes present in the microbial extract. Performing synthesis with extracts from genetically modified microbial strains that are deficient in multiple amino acid metabolizing enzymes reduces the enzymatic activities responsible for catalyzing these deleterious reactions and improves the overall yield of synthesis.

In one embodiment of the invention, a bacterial strain is provided in which multiple genetic deletions have been made in enzymes affecting amino acid metabolism. In such strains, at least two, three, four, five or more genes are "knocked out", where synthesis of the targeted enzyme is substantially absent, through deletion of all or part of the coding sequence; deletion of all or part of the relevant promoter or operator sequence; introduction of one or more stop codons at a position in the coding sequence that will substantially ablate expression; and the like. The use of E. coli is of particular interest, where the deletions usually comprise at least two of speA, tnaA, sdaA, sdaB, and gshA. Additional genetic modifications may also be made to the microbial strain, for example the deletion of tonA and endA genes to protect against bacteriophage infection and stabilize DNA within the system.

In another embodiment of the invention, a cellular extract of a bacterial strain as described above is provided, which extract may be provided in a fresh or frozen form, and may further be formulated into a reaction mix suitable for polypeptide synthesis. Such extracts are obtained by any of the methods known in the art for the purpose of cell-free protein synthesis. In one example of such methods, cells are grown in media to the appropriate optical density, harvested by centrifugation and washed in S30 buffer (10 mM Tris, 8.2, 14 mM Mg acetate, 60 mM potassium acetate, 1 mM DTT). After the final wash, the cells are resuspended in S30 buffer and disrupted, e.g. with a French press. The lysate is then centrifuged, and the withdrawn supernatant used as the extract. The extract is optionally further purified by dialysis, centrifugation, dilution with appropriate salts, and the like. Methods for producing active extracts are known in the art, for example they may be found in Pratt (1984), coupled transcription-translation in prokaryotic cell-free systems, p. 179-209, in Hames, B. D. and Higgins, S. J. (ed.), Transcription and Translation: a practical approach, IRL Press, New York. Kudlicki et al. (1992) *Anal Biochem* 206(2):389-93 modify the S30 *E. coli* cell-free extract by collecting the ribosome fraction from the S30 by ultracentrifugation.

The extracts may be optimized for expression of genes under control of a specific promoter, (for example see Nevin and Pratt (1991) FEBS Left 291(2):259-63, which system consists of an *E. coli* crude extract (prepared from cells containing endogenous T7 RNA polymerase) and rifampicin (an *E. coli* RNA polymerase inhibitor)). Kim et al. (1996) Eur. J. Biochem. 239: 881-886 further enhance protein production by optimizing reagent concentrations.

In another embodiment of the invention, methods of cell-free polypeptide synthesis are provided, where the reaction mixture comprises a cell extract as described above. Surprisingly, it is shown herein that bacteria containing such multiple deletions can be grown, and provide a useful extract for cell-free synthesis. By the use of such a cell extract, the cell-free reaction can be performed in a batch mode for up to three hours while maintaining all 20 amino acids at significant levels, for example at greater than 1 mM concentration, throughout the reaction.

The cell-free system offers a flexible format for protein expression. This flexibility allows for numerous modifications to the compositions of the system without adversely affecting the advantages gained by this new technology.

As described above, the coding sequence for multiple endogenous enzymes are "knocked-out" or otherwise inactivated in the chromosome of the source organism, by deletion of all or a part of the coding sequence; frame-shift insertion; dominant negative mutations, etc. The genomes of a number of organisms, including *E. coli,* have been completely sequenced, thereby facilitating the genetic modifications. For example, a markerless knockout strategy method is described by Arigoni et al. (1998) *Nat Biotechnol* 16(9):851-6. Mutations can be combined in a single organism through known techniques of gene transfer.

A preferred method for inactivating targeted genes is described by Hoang et al. (1998) *Gene* 212:77-86. In this method, gene replacement vectors are employed that contain a tetracycline resistance gene and a gene encoding levan sucrase (sacB) as selection markers for recombination. The target gene is first cloned and mutagenized, preferably by deleting a significant portion of the gene. This gene is then inserted by ligation into a vector designed for facilitating chromosomal gene replacement. The *E. coli* cells are then transformed with those vectors. Cells that have incorporated the plasmid into the chromosome at the site of the target gene are selected, then the plasmid is forced to leave the chromosome by growing the cells on sucrose. Sucrose is toxic when the sacB gene resides in the chromosome. The properly mutated strain is selected based on its phenotype of tetracycline sensitivity and sucrose resistance. PCR analysis or DNA sequencing then confirms the desired genetic change. Alternatively, the method described by Datsenko and Wanner (2000) may be used, as shown in Example 1.

However, in some cases the enzyme reducing the duration and yield of the protein synthesis reaction may be essential for the growth of the source organism. In those cases, a conditional knock-out may be used. For example, anti-sense sequences corresponding to the targeted gene are introduced into the source organism on an inducible promoter. The cells are grown for a period of time, and then the anti-sense construct induced, in order to deplete the cell of the targeted enzyme.

Genes of interest for deletion include the tryptophanase gene (tnaA) of *E. coli,* which sequence may be found in Deely and Yanofsky (1981) *J. Bact.* 147: 787-796; Genbank accession no. 1790144; locus AE000448, accession AE000448 of *E. coli* complete genome sequence. Using publicly available genetic sequences, the activity of the tryptophanase may be inactivated in a modified bacterial cell, as described above.

The arginine decarboxylase (speA) gene of *E. coli* may also be inactivated. The genetic sequence may be accessed through Genbank, no. 1789307; locus AE000377, accession AE000377. The complete chromosomal sequence of *E. coli* has been published in Blattner et al. (1997) Science 277: 1453-1474. As described above, the gene may be inactivated, or the protein product otherwise depleted from the reaction mixture.

The L-serine deaminase genes, sdaA and sdaB may also be inactivated. The sequence of these genes is described by Shao and Newman E. B. (1993) Eur J Biochem 212:777-784; and Su et al. (1989) J Bacteriol 171:5095-5102. The genetic sequences may also be obtained from public databases, such as Genbank accession AE000448 of *E. coli* complete genome sequence.

The gamma-glutamylcysteine synthase gene, gshA, may also be inactivated. The sequence of this gene is described by Murata and Kimura (1982) Appl Environ Microbiol 44:1444-8. The genetic sequences may also be obtained from public databases, such as Genbank accession AE000448 of *E. coli* complete genome sequence.

Cell-free synthesis, as used herein, refers to the cell-free synthesis of biological macromolecules in a reaction mix comprising biological extracts and/or defined reagents. The reaction mix will comprise a template for production of the macromolecule, e.g. DNA, mRNA, etc.; monomers for the macromolecule to be synthesized, e.g. amino acids, etc., and such co-factors, enzymes and other reagents that are necessary for the synthesis, e.g. ribosomes, tRNA, polymerases, transcriptional factors, etc., many of which are provided by the microbial cell extract. Such synthetic reaction systems are well-known in the art, and have been described in the literature. For example, reaction chemistries are described in U.S. Pat. No. 6,337,191, issued Jan. 8, 2002, and U.S. Pat. No. 6,168,931, issued Jan. 2, 2001, herein incorporated by reference. The system can be run under aerobic and anaerobic conditions. It is not necessary to add exogenous cofactors for this new technology. Compounds such as nicotinamide adenine dinucleotide (NADH or $NAD^+$) or coenzyme A can be used to supplement protein synthesis yields but are not required.

In one embodiment of the invention, the reaction chemistry is as described in International Application WO 2004/016778, herein incorporated by reference. Oxidative phosphorylation is activated, providing for increased yields and enhanced utilization of energy sources. Improved yield is obtained by a combination of factors, including the use of biological extracts derived from bacteria grown on a glucose containing medium; an absence of polyethylene glycol; and optimized magnesium concentration. This provides for a homeostatic system, in which synthesis can occur even in the absence of secondary energy sources.

The compositions and methods of this invention allow for production of proteins with any secondary energy source used to energize synthesis. These can include but are not limited to glycolytic intermediates, such as glucose, pyruvate, or acetate. Other glycolytic intermediates, such as glucose-6-phosphate, fructose-6-phosphate, fructose-1,6-diphosphate, triose phosphate, 3-phosphoglycerate, 2-phosphoglycerate, and phosphoenolpyruvate (PEP), are already phosphorylated, so they may not be susceptible to phosphate limitation. Any compound used to generate reduction equivalents or to activate a pathway that may generate reduction equivalents may also be added. These compounds include amino acids (particularly glutamate), tricarboxylic acid (TCA) cycle intermediates (citrate, cis-aconitate, isocitrate, α-ketoglutarate, succinyl-CoA, succinate, fumarate, malate, and oxaloacetate), or other molecules that can be directed into central metabolism (such as glyoxylate). In addition, vesicles containing respiratory chain components may also be added to assist in energy generation. The energy source may be supplied in concentrations around 30 mM. The secondary energy sources are not usually added in concentrations greater than 150 mM. Additional amounts of the energy source may be added to the reaction mixture during the course of protein expression to fuel longer reaction times.

Addition of oxalic acid, a metabolic inhibitor to phosphoenolpyruvate synthetase, is beneficial in increasing protein yields, for example, in PEP- or glutamate-based systems. However, the addition of oxalic acid is inhibitory when using glucose or glucose-6-phosphate as the energy source, and thus can be removed from the reaction when using these energy sources.

The template for cell-free protein synthesis can be either mRNA or DNA. Translation of stabilized mRNA or combined transcription and translation converts stored information into protein. The combined system, generally utilized in *E. coli* systems, continuously generates mRNA from a DNA template with a recognizable promoter. Either endogenous RNA polymerase is used, or an exogenous phage RNA polymerase, typically T7 or SP6, is added directly to the reaction mixture. Alternatively, mRNA can be continually amplified by inserting the message into a template for QB replicase, an RNA dependent RNA polymerase. Purified mRNA is generally stabilized by chemical modification before it is added to the reaction mixture. Nucleases can be removed from extracts to help stabilize mRNA levels. The template can encode for any particular gene of interest.

Other salts, particularly those that are biologically relevant, such as manganese, may also be added. Potassium is generally added between 50-250 mM and ammonium between 0-100 mM. The pH of the reaction is generally run between pH 6-9. The temperature of the reaction is generally between 20° C. and 40° C. These ranges may be extended.

Metabolic inhibitors to undesirable enzymatic activity may be added to the reaction mixture. Alternatively, enzymes or factors that are responsible for undesirable activity may be removed directly from the extract or the gene encoding the undesirable enzyme may be inactivated or deleted from the chromosome.

Vesicles, either purified from the host organism or synthetic, may also be added to the system. These may be used to enhance protein synthesis and folding. This cytomim technology has been shown to activate processes that utilize membrane vesicles containing respiratory chain components for the activation of oxidative phosphorylation. The present methods may be used for cell-free expression to activate other sets of membrane proteins.

The reactions may be large scale, small scale, or may be multiplexed to perform a plurality of simultaneous syntheses. Additional reagents may be introduced to prolong the period of time for active synthesis. Synthesized product is usually accumulated in the reactor, and then is isolated and purified according to the usual methods for protein purification after completion of the system operation.

Of particular interest is the translation of mRNA to produce proteins, which translation may be coupled to in vitro synthesis of mRNA from a DNA template. Such a cell-free system will contain all factors required for the translation of mRNA, for example ribosomes, amino acids, tRNAs, aminoacyl synthetases, elongation factors and initiation factors. Cell-free systems known in the art include *E. coli* extracts, etc., which can be treated with a suitable nuclease to eliminate active endogenous mRNA.

In addition to the above components such as cell-free extract, genetic template, and amino acids, materials specifically required for protein synthesis may be added to the reaction. These materials include salts, polymeric compounds, cyclic AMP, inhibitors for protein or nucleic acid degrading enzymes, inhibitors or regulators of protein synthesis, oxidation/reduction adjusters, non-denaturing surfactants, buffer components, spermine, spermidine, putrescine, etc.

The salts preferably include potassium, magnesium, ammonium and manganese salts of acetic acid or sulfuric acid, and some of these may have amino acids as a counter anion. The polymeric compounds may be polyethylene glycol, dextran, diethyl aminoethyl dextran, quaternary aminoethyl and aminoethyl dextran, etc. The oxidation/reduction adjuster may be dithiothreitol, ascorbic acid, glutathione and/or their oxides. Also, a non-denaturing surfactant such as Triton X-100 may be used at a concentration of 0-0.5 M. Spermine, spermidine, or putrescine may be used for improving protein synthetic ability, and cAMP may be used as a gene expression regulator.

When changing the concentration of a particular component of the reaction medium, that of another component may be changed accordingly. For example, the concentrations of several components such as nucleotides and energy source compounds may be simultaneously controlled in accordance with the change in those of other components. Also, the concentration levels of components in the reactor may be varied over time.

Preferably, the reaction is maintained in the range of pH 5-10 and a temperature of 20°-50° C., and more preferably, in the range of pH 6-9 and a temperature of 25°-40° C.

The amount of protein produced in a translation reaction can be measured in various fashions. One method relies on the availability of an assay that measures the activity of the particular protein being translated. Examples of assays for measuring protein activity are a luciferase assay system, and a chloramphenical acetyl transferase assay system. These assays measure the amount of functionally active protein produced from the translation reaction. Activity assays will not measure full-length protein that is inactive due to improper protein folding or lack of other post translational modifications necessary for protein activity.

Another method of measuring the amount of protein produced in a combined in vitro transcription and translation reactions is to perform the reactions using a known quantity of radiolabeled amino acid such as $^{35}$S-methionine or $^{14}$C-leucine and subsequently measuring the amount of radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

The standard cell-free reaction mixture used for the coupled transcription-translation reaction is the PANOxSP system as described by Jewett, M. C., and Swartz, J. R. (2004) *Biotechnol Bioeng* 86, 19-26 with slight modifications. The specific components of the reaction include 30 mM PEP, 1.2 mM ATP, 0.86 mM each of GTP, UTP, and CTP, 130 mM potassium glutamate, 10 mM ammonium glutamate, 16 mM magnesium glutamate, 34 µg/mL folinic acid, 170.6 µg/mL *E. coli* tRNA mixture, 13.3 µg/mL plasmid, 50 mM HEPES (pH 7.5), 1.5 mM spermidine, 1 mM putrescine, 2 mM each of 20 unlabeled amino acids, 5 µM [$^{14}$C]-Leucine, 0.33 mM nicotinamide adenine dinucleotide, 0.26 mM coenzyme A, 2.7 mM sodium oxalate and 0.24 volumes of *E. coli* S30 extract.

The cell-free protein synthesis reaction is performed with a crude S30 extract derived from various *E. coli* strains. These A19 derivatives have genotypes as listed in Table I. Several of the deleted genes code for enzymes directly responsible for amino acid degradation (Table II). The gene deletion protocol was adapted from the method of Datsenko and Wanner, (2000) *Proc Natl Acad Sci USA* 97, 6640-5 and is described for all except the ΔgshA deletion by Michel-Reydellet et al. (2004) *Metab Eng* 6, 197-203. The final deletion of gene gshA was also performed using the Datsenko and Wanner method.

TABLE I

Genotypes of cell strains KC1 and KC6 developed to stabilize amino acid concentrations during cell-free protein synthesis.

| Strain | Genotype | Amino Acids Stabilized |
|---|---|---|
| A19 | Rna-19gshA2his-95*relA1spoT1metB1 | None |
| NMR1 | A19 ΔendA met$^+$ | None |
| KC1 | A19 ΔtonA ΔtnaA ΔspeA ΔendA ΔsdaA ΔsdaB met$^+$ | Arg, Trp, Ser |
| KC6 | A19 ΔtonA ΔtnaA ΔspeA ΔendA ΔsdaA ΔsdaB ΔgshA met$^+$ | Arg, Trp, Ser, Cys |

*The A19 strain in our laboratory has reverted to histidine prototrophy.

TABLE II

Amino acids requiring stabilization during cell-free protein synthesis reaction, the related harmful enzymatic activity, and the reaction catalyzed by that enzyme.

| Amino Acid | Enzyme (gene) | Reaction |
|---|---|---|
| Tryptophan | Trptophanase (tnaA) | L-tryptophan + $H_2O$ → indole + pyruvate + $NH_3$ <br> L-serine → pyruvate + $NH_3$ <br> L-cysteine + $H_2O$ → pyruvate + $NH_3$ + $H_2S$ |
| Arginine | Arginine decarboxylase (speA) | Arginine → agamatine + $CO_2$ |
| Serine | Serine deaminase (sdaA, sdaB) | L-serine → pyruvate + $NH_3$ |
| Cysteine | Glutamate-cysteine ligase (gshA) | L-cysteine + L-glutamate + ATP → γ-glutamylcysteine + ADP + $P_i$ |

Extract preparation was performed as described previously by Jewett et al. (2002) in *Gene cloning and expression technologies* (Weiner, M., and Lu, Q., Eds.) pp 391-411, Eaton Publishing, Westborough, Mass. Plasmid pK7CAT or pK7OmpT was used as a template for protein synthesis. pK7CAT encodes for the sequence of chloramphenicol acetyl transferase (CAT) using the T7 promoter and terminator. PK7OmpT encodes for the sequence of outer membrane protein T (OmpT) also using the T7 promoter and terminator. T7 polymerase, prepared as described by Davenloo (1984), was added to the reaction at a final concentration of 70 µg/ml. The amount of synthesized protein is calculated from the TCA-insoluble radioactivity measured with a liquid scintillation counter.

To verify that the gene deletions stabilized amino acid levels, samples from cell-free reactions using the various extracts were analyzed with HPLC. The Dionex (Sunneyvale, Calif.) Amino Acid Analysis System separates amino acids by gradient anion exchange and uses pulsed electrochemical detection. The samples were prepared by adding 15 µl of 150 mM sulfuric acid to 15 µL of cell-free reaction mixture to precipitate protein. The sample is centrifuged for 10 minutes at 12000 g and 4° C. The sample was further diluted 1:100 with sulfuric acid (0.4 M final concentration) to give a diluted amino acid concentration for initial reaction mixtures of approximately 10 µM.

Figure 2B:
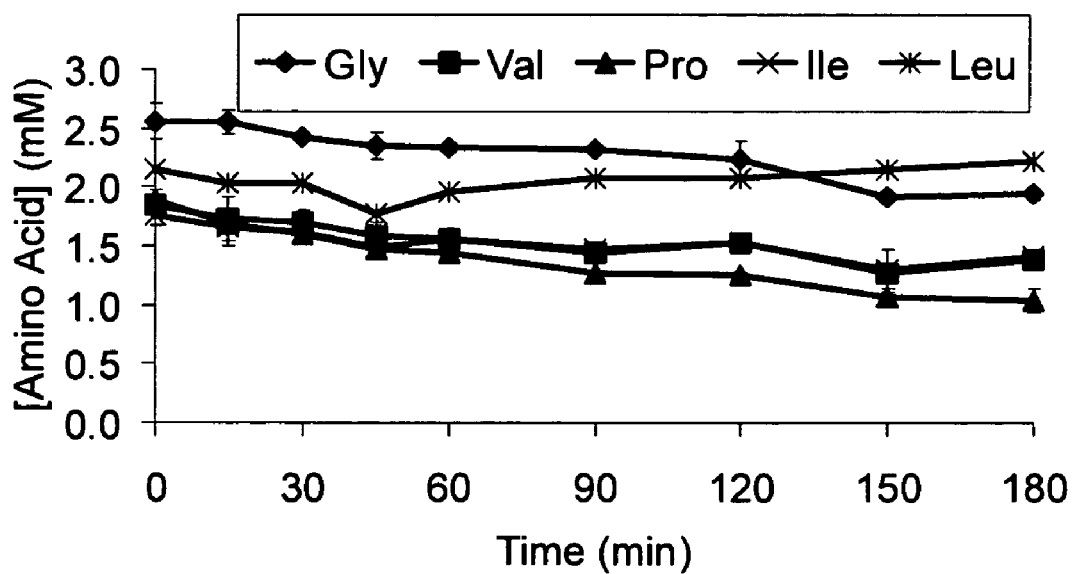

The amino acid concentrations of arginine, tryptophan, serine, and cysteine are stabilized in the extracts with the gene deletions (FIG. 1A-D). In addition, the remaining amino acids are also stable at significant levels (>1 mM) throughout the cell-free reaction (FIG. 2A-C). Glutamate is not included in these graphs since it is present in high concentration (156 mM) from the reaction salts.

Figure 3:
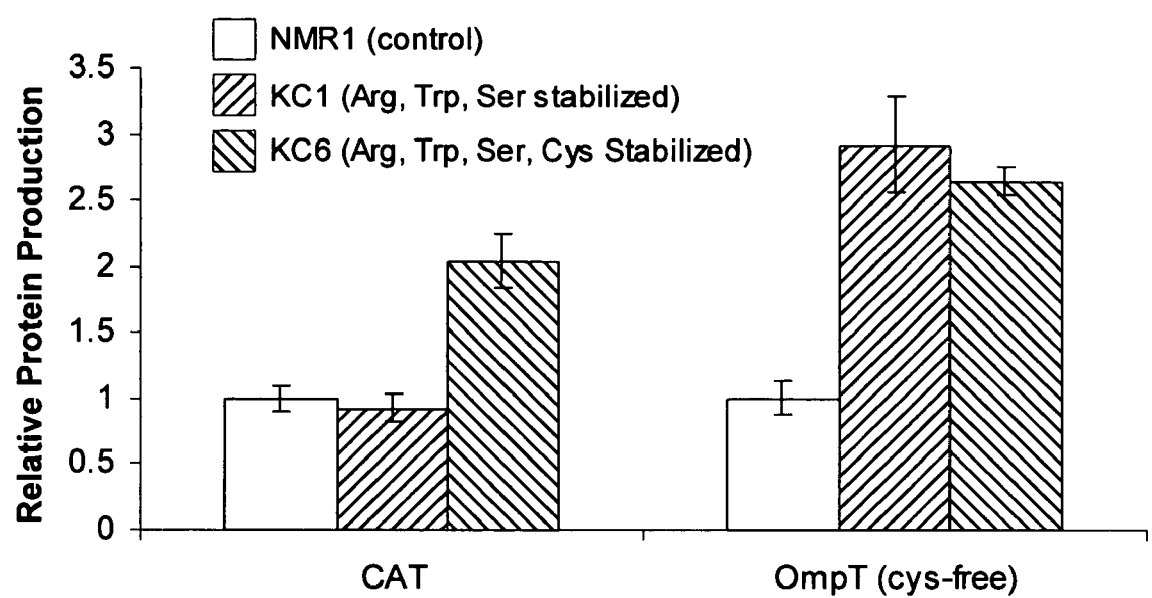
FIG. 3: Relative protein synthesis yields for cell-free reactions producing CAT protein or OmpT protein.

The protein synthesis yields in a cell-free reaction improved over 2 times when using the KC6 strain (FIG. 3). This improvement is most pronounced when using a starting amino acid concentration of 0.5 mM.

Previously, cell-free protein synthesis reactions were limited by the depletion of a critical substrate, the amino acids, during the reaction. The ability to control amino acid depletion through deletions of genes in the source strain used to make cell extract represents a substantial improvement over existing methods. The above data demonstrate stabilization of all 20 amino acids through this technique. The deletion of 5 genes (speA, tnaA, sdaA, sdaB, and gshA) did not adversely affect the growth of the cells used to make extract or the activity of the extract itself.

Removing unwanted enzymatic activity through gene deletions may have advantages over the use of inhibitors or substrate-feeding approaches, which could affect other necessary activities in the extract, or are cumbersome and expensive. The use of genetically engineered organisms as a source of extracts is a simple, efficient way to stabilize amino acids for cell-free protein synthesis reactions.

What is claimed is:

1. A S30 cell-free extract of an *E. coli* bacterial cell, wherein said bacterial cell comprises inactivated genes for tryptophanase, arginine decarboxylase, L-serine deaminase and gamma-glutamylcysteine synthase.

2. A S30 cell-free extract of *E. coli*, wherein the *E. coli* cell comprises inactivated genes in tnaA, speA, sdaA, sdaB and gshA.

3. The S30 extract of claim 1, wherein said extract is provided in a reaction mixture suitable for cell-free polypeptide synthesis.

4. The reaction mixture of claim 3, wherein levels of all 20 amino acids are maintained during cell-free synthesis reactions.

5. An *E. coli* bacterial cell, wherein said bacterial cell comprises inactivated genes for tryptophanase, arginine decarboxylase, L-serine deaminase and gamma-glutamylcysteine synthase.

6. An *E. coli*, wherein the *E. coli* cell comprises inactivated genes in tnaA, speA, sdaA, sdaB and gshA.

7. A method of cell-free polypeptide synthesis, the method comprising:
    incubating a polynucleotide encoding a polypeptide of interest in a reaction mixture comprising a S30 cell-free extract according to claim 1 or claim 2 for a period of time sufficient to synthesize said polypeptide.

8. The method according to claim 7, wherein levels of all 20 amino acids are maintained during cell-free synthesis reactions.

* * * * *